US00PP13718P29

(12) United States Plant Patent
Olsthoorn

(10) Patent No.: US PP13,718 P2
(45) Date of Patent: Apr. 8, 2003

(54) SPATHIPHYLLUM PLANT NAMED '54905'

(75) Inventor: Petrus C. M. Olsthoorn, Monster (NL)

(73) Assignee: Pothos Plant B.V., Honselersdijk (NL)

( * ) Notice: Subject to any disclaimer, the term of this patent is extended or adjusted under 35 U.S.C. 154(b) by 0 days.

(21) Appl. No.: 10/076,343

(22) Filed: Feb. 19, 2002

(51) Int. Cl.[7] ..... A01H 5/00

(52) U.S. Cl. ..... Plt./364
(58) Field of Search ..... Plt./364

*Primary Examiner*—Bruce R. Campell
*Assistant Examiner*—June Hwu
(74) *Attorney, Agent, or Firm*—Foley & Lardner

(57) ABSTRACT

A new and distinct Spathiphyllum plant named '54905' characterized by early shoot production, dark green leaves, round inflorescences, high inflorescence production, and compact plant size.

2 Drawing Sheets

LATIN NAMED OF THE GENUS AND SPECIES OF THE PLANT CLAIMED

Spathiphyllum hybrid.

VARIETY DENOMINATION

'54905'.

BACKGROUND OF THE INVENTION

The present invention relates to a new and distinct cultivar of Spathiphyllum plant, hereinafter referred to by the cultivar name '54905'.

The new cultivar originated from a cross made in a controlled breeding program in Monster, The Netherlands. The female parent is '91317-4' (unpatented). The male parent is '91188-9' (unpatented). '54905' was discovered and selected by the inventor, Petrus C.M. Olsthoorn, as a flowering plant within the progeny of the stated cross in a controlled environment in Monster, The Netherlands.

Asexual reproduction of the new cultivar by leaf-cutting was first performed by tissue culture in week 49 of 1995 in Honselersdijk, The Netherlands and has demonstrated that the combination of characteristics as herein disclosed for the new cultivar are firmly fixed and retained through successive generations of asexual reproduction and reproduce true-to-type.

BRIEF DESCRIPTION OF THE INVENTION

The following traits have been repeatedly observed and are determined to be basic characteristics of '54905' which in combination distinguish this Spathiphyllum as a new and distinct cultivar:

1. Early shoot production;
2. Dark green leaves;
3. Round inflorescences;
4. High inflorescence production; and
5. Compact plant size.

'54905' has not been observed under all possible environmental conditions. The phenotype of the new cultivar may vary significantly with variations in environment such as temperature, light intensity, and day length without any change in the genotype of the plant. The following observations, measurements and values describe the new cultivar as grown in Honselersdijk, The Netherlands under conditions which closely approximate those generally used in commercial practice.

Of the many commercial cultivars known to the present inventor, the most similar in comparison to '54905' is the cultivar 'Cupido' (unpatented). '54905' produces shoots early; within fifteen weeks after tissue culture the first shoot appears. '54905' has darker leaves than 'Cupido'. The inflorescence of '54905' are rounder than those of 'Cupido'. '54905' produces 7–15 inflorescences (depending on pot size) whereas 'Cupido' produces 8–10. '54905' produces up to 7 inflorescences at once whereas 'Cupido' produces only 2–3 inflorescences at once. The plant height of '54905' is approximately 60 percent that of 'Cupido'. The leaves of '54905' are narrower than the leaves of 'Cupido'. The leaf and inflorescence margins of '54905' are undulate whereas the leaf and inflorescence margins of 'Cupido' are entire. 'Cupido' is more sensitive to light than '54905', causing leaves of 'Cupido' to lighten in color faster. Finally, in order to get the shoots of a Spathiphyllum to flower, gibberalic acid is added. 'Cupido' needs more than twice the concentration of this hormone than '54905' to get the same result.

BRIEF DESCRIPTION OF THE DRAWINGS

The accompanying photographic drawings show a 23-week old plant of '54905'.

The first drawing shows a '54905' plant on the left and a close up of its inflorescence on the right.

The second drawing shows a '54905' plant on the left with a prior art 'Cupido' plant on the right.

DETAILED BOTANICAL DESCRIPTION

The following observations, measurements and values describe the new cultivar at 23 weeks as grown in Honselersdijk, The Netherlands under conditions which closely approximate those generally used in commercial practice. Grown in standard glasshouses in well-drained cocos, pH values in cocos/peat soil (50/50) is 6.0–6.2 and 5.8–6.0 in potting soil. Base fertilizing (PG-mix) is 0.75 kgs in cocos/peat soil as well as in potting soil. This species needs careful fertilizer treatment; mixes of calcium nitrate, iron chelate (EDDHA and DTPA), magnesium sulphate, mono potassium phospate, potassium nitrate, borax, manganese, molybdenum and copper sulphate. Ideal growing conditions under which this plant is grown is 21–23 degrees Celsius during the day and 20 degrees Celsius at night. For flower initiation '54905' gets 40 ppm of gibberalic acid (depending on the pot size, plant development and age of plant).

Color references are made to The Royal Horticultural Society Colour Chart (R.H.S.), except where general colors of ordinary significance are used. Color values were taken under daylight conditions at approximately noon in Boskoop, The Netherlands.

Origin: Honselersdijk, The Netherlands, November 2001.
Parentage:
*Male parent.*—'91317-4'.
*Female parent.*—'91188-9'.
Classification:
*Botanical.*—Spathiphyllum.
*Commercial.*—Spathiphyllum c.v. '54905'.
Propagation: By tissue culture.
Plant:
*Appearance.*—Broad and upright with leaf petioles growing directly from base.
*Height.*—Average 30 cm (excluding flowers).
*Width.*—Average 60 cm.
*Growth habit.*—Moderately vigorous. Winter Hardiness: USDA Zone 10.
*Stems.*—Leaves grow directly from base, so no stems are visible.
*Roots.*—Time to initiate roots: 1–2 weeks under 21–23 degrees Celsius (day) and 20 degrees Celsius at night. Time to develop roots: 3–4 weeks under 21–23 degrees Celsius (day) and 20 degrees Celsius at night. Rooting habit: Freely branching.
Foliage:
*Shape.*—Narrow elliptic to lanceolate.
*Apex.*—Narrow acute to slightly apiculate.
*Base.*—Attenuate.
*Texture.*—Smooth, glossy, somewhat leathery.
*Leaf color.*—Upper surface: Green to yellow-green closest to but darker than RHS 139A to RHS 147A. Lower surface: Green RHS 137B.
*Midrib color.*—Upper Surface: Green, darker than but closest to RHS 143A. Lower Surface: Yellow-green RHS 144B.
*Size of leaf.*—Width: Average 8.5 cm. Length: Average 24 cm. Petiole: Average length 14 cm, average diameter 3 mm, rounded, color green RHS 143B to RHS 143C.
*Petiole sheath.*—Average 13 cm long and 8 mm wide (measured at halfway point).
*Geniculum.*—Average length 1.5 cm, average width 4 mm, color green RHS 143A.
*Veins.*—Average 10 pairs of furrowed secondary veins, upper side color is darker than but closest to green to yellow-green RHS 139A to RHS 147A, under side green RHS 143B.
Inflorescence description:
*Immature.*—Peduncle: Average length 39 cm, average diameter 4 mm, rounded, color green RHS 143A to RHS 143B. Spathe: Average length 12 cm, average width 4.5 cm, cupped, average depth 1.2 cm.
*Mature.*—Spathe: Size: Average length 13 cm, average width 5 cm, cupped, average depth 1.2 cm. Color: Unopened Bud: White, closest color between RHS 155A and RHS 157D. Base shape: Decurrent. Fully Open: Front Surface: White closest to RHS 155A, midrib green-white RHS 157A. Back Surface: White, closes to RHS 155A, midrib green RHS 143A to RHS 143B. Apex: Apiculate, green RHS 143B to RHS 143D. Faded: Front Surface: Yellow-green RHS 145D, turning to brown RHS 199A with age. Back Surface: Yellow-green RHS 145C to RHS 145D, turning to brown RHS 199A to RHS 199B with age. Apex: Green RHS 143A to RHS 143B.
*Arrangement.*—Solitary.
*Shape.*—Broad lanceolate.
*Margins.*—Entire, slightly wavy.
*Fragrance.*—Sweet, pleasant.
*Lastingness of the individual inflorescence.*—On average over two weeks.
*Time of flowering.*—23 weeks after potting of 27 cm cutting.
Reproductive organs:
*Spadix.*—Size: Average length 2.5 cm, average width 1.1 cm. Quantity: Average 60 individual flowers per spadix. Color: Greyed-yellow RHS 160D. Stamens: 6, pressed against styles. Pistil: Each individual flower has one pistil with a tri-parted stigma; the pistil has an average length of 2 mm, color is greyed-yellow RHS 160D.
*Pollen.*—Yellow-white RHS 158A.
Seed production: No observations to date.
Fruit production: No observations to date.
Disease resistance/susceptibility: No observations to date.

I claim:

1. A new and distinct Spathiphyllum plant named '54905', substantially as illustrated and described herein.

* * * * *

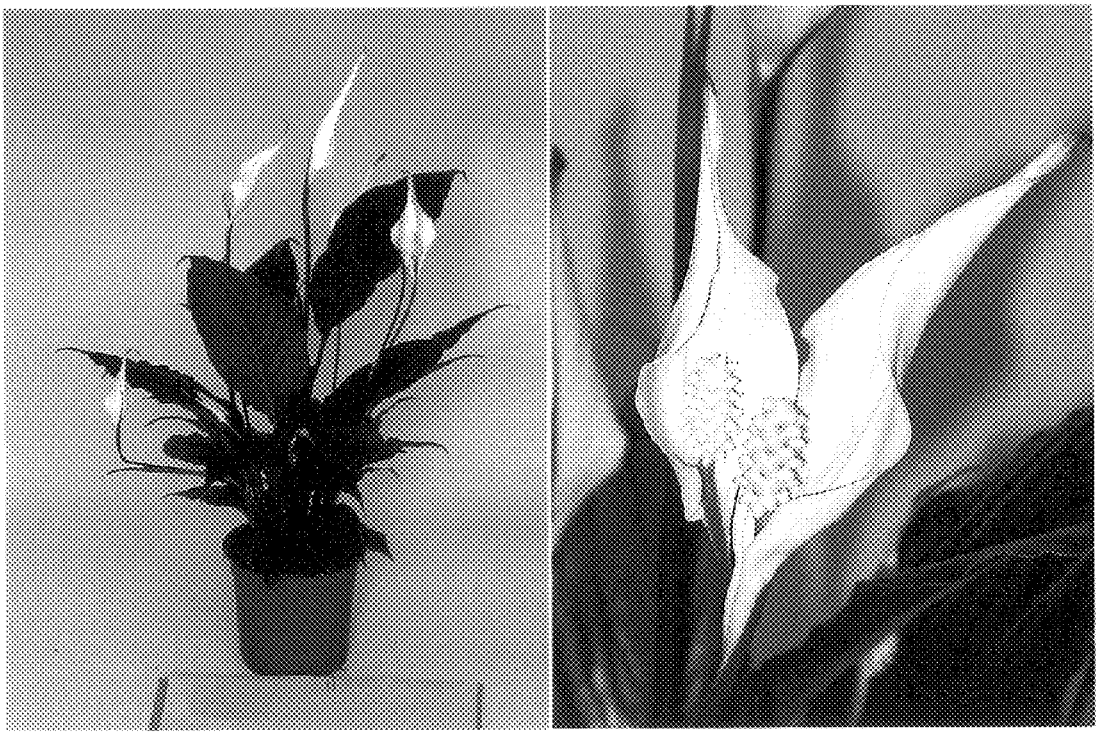

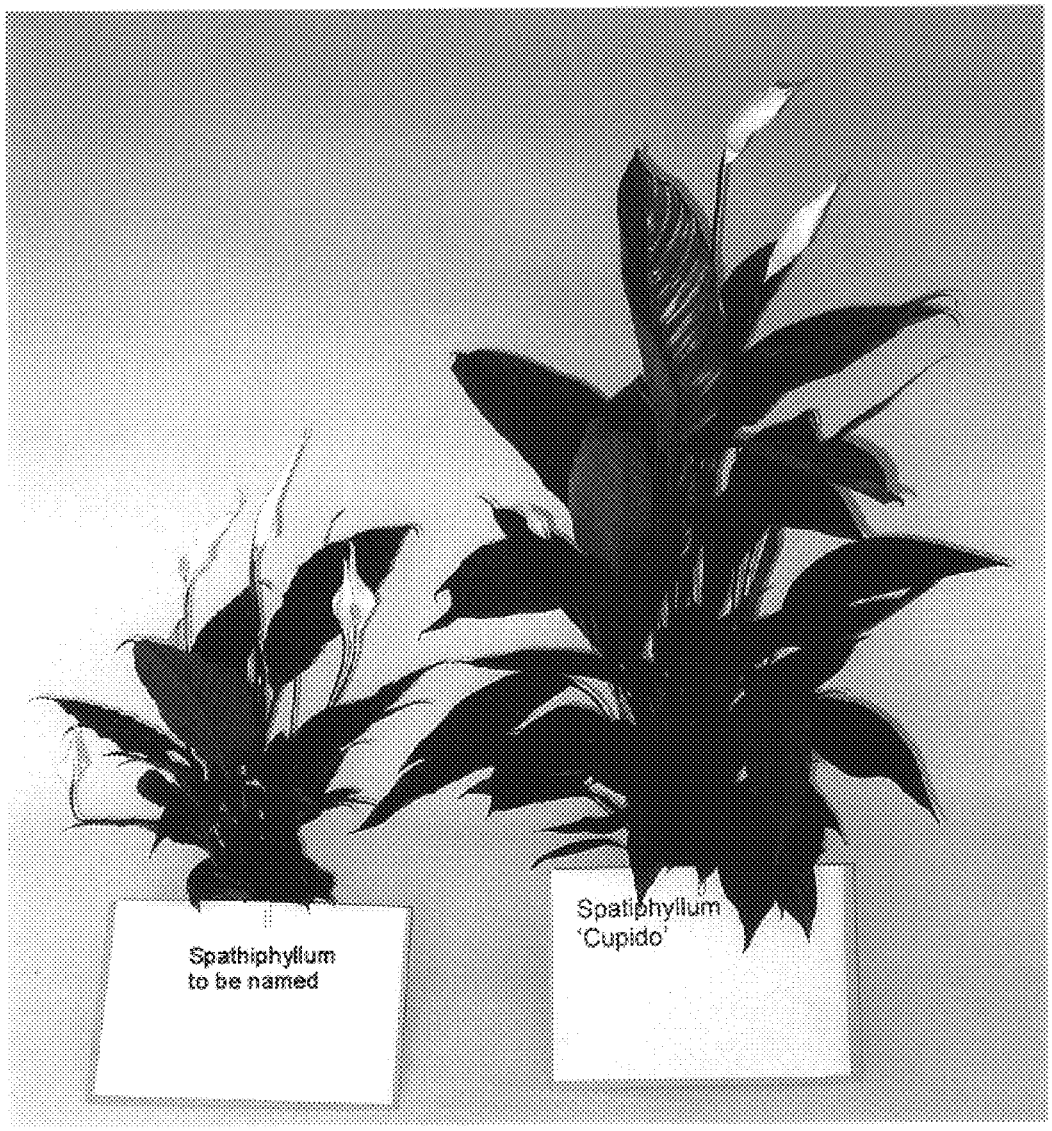
Spathiphyllum
to be named
Spatiphyllum
'Cupido'